United States Patent
Shivashankar et al.

(10) Patent No.: US 6,489,106 B1
(45) Date of Patent: Dec. 3, 2002

(54) CONTROL OF THE EXPRESSION OF ANCHORED GENES USING MICRON SCALE HEATERS

(75) Inventors: G. V. Shivashankar, Bangalore (IN); Shumo Liu, Princeton, NJ (US); Albert J. Libchaber, New York, NY (US)

(73) Assignee: NEC Research Institute, Inc., Princeton, NJ (US)

( * ) Notice: Subject to any disclaimer, the term of this patent is extended or adjusted under 35 U.S.C. 154(b) by 0 days.

(21) Appl. No.: 09/523,578

(22) Filed: Mar. 10, 2000

(51) Int. Cl.$^7$ .................. C12Q 1/68; C12P 19/34; C12M 1/34; C07H 21/02; C07H 21/04
(52) U.S. Cl. .................. 435/6; 435/91.1; 435/91.2; 435/285.2; 435/287.2; 536/22.1; 536/23.1; 536/24.1; 536/24.2; 536/24.3; 536/24.33
(58) Field of Search .................. 435/6, 7.1, 91.1, 435/91.2, 285.2, 287.2; 536/22.1, 23.1, 24.1, 24.2, 24.3, 24.31, 24.32, 29–33

(56) References Cited

U.S. PATENT DOCUMENTS

| | | | |
|---|---|---|---|
| 6,001,568 A | * 12/1999 | Chetverin et al. | 435/6 |
| 6,090,553 A | * 7/2000 | Matson | 435/6 |
| 6,107,452 A | * 8/2000 | Miller et al. | 528/422 |
| 6,218,126 B1 | * 4/2001 | Yasuda et al. | 435/6 |
| 6,238,862 B1 | * 5/2001 | McGall | 435/6 |

OTHER PUBLICATIONS

Federov et al PNAS vol. 92, pp. 1227–1231 Feb. 1995.*
Alberts, B. et al., "Chapter 9: Control of Gene Expression", *Molecular Biology Of The Cell*, Third Edition, 401–432(1983).
Jermutus, L. et al., "Recent adcances in producing and selecting functional proteins by using cell–free translation", *Current Opinion in Biotechnology*, vol. 9: 534–548 (1998).
Lander, E.S., "Array of Hope", *Perspective: Nature Genetics, suppl: 1–8*, pp. 3–4 (1999).
Makeyev, E. V. et al., "Enzymatic activity of the ribosome-bound nascent polypeptide", *FEBS Letters*, vol. 378: 166–170 (1996).
Olson, M. V., "The human genome project", *Proc. Natl. Acad. Sci. USA*, vol. 90: 4338–4344 (1993).
Southern, E. et al., "Molecular interactions on microarrays", *Nature Genetics Supplement*, vol. 21: 5–9 (1999).
Wilson, T. et al., "Bioluminescence", *Annu. Rev. Cell Dev. Biol.*, vol. 14: 197–230 (1998).
Kolb, V.A. et al., "Folding of firefly luciferase during translation in a cell–free system", *The EMBO Journal*, vol. 13(15): 3631–3637 (1994).
Shivashankar, G. V. et al., "Biomaolecular recognition using submicron laser lithography", *Applied Physics Letters*, vol. 73(3): 417–419 (1998).

* cited by examiner

Primary Examiner—Jeffrey Siew
(74) Attorney, Agent, or Firm—Scully, Scott, Murphy & Presser (57) ABSTRACT

The present invention demonstrates that gene expression can be controlled in vitro using DNA (gene) sequences immobilized on a template with micron scale temperature heaters. Such expression is controllable by varying temperature of the template on a short time scale. The present invention further demonstrates that nucleic acid constructs controlled by the present method express protein either free or bound to the nucleic acid. Based on these findings, the present invention provides methods and apparatuses useful for the preparation of in vitro programmable protein networks and protein micro arrays.

30 Claims, 12 Drawing Sheets

CONTROL OF THE EXPRESSION OF ANCHORED GENES USING MICRON SCALE HEATERS

FIELD OF THE INVENTION

The present invention relates to methods and products for controlling the expression of genes immobilized on a temperature controlled template. More particularly, the invention relates to the use of an in vitro method and apparatus for controlling gene expression.

BACKGROUND OF THE INVENTION

Gene expression is controlled by a variety of regulatory mechanisms (Alberts B, et al. (1994) "Molecular Biology of the Cell" New York, Garland). Advances in genome sequencing (Olson M. V. (1993) Proc. Natl. Acad. Sci. 90:4338–4344) and DNA chips ("DNA chips" (1999) Special Issue, Nature Genetics, suppl. vol. 21, January, 1999) provide insight into the collective gene expression pattern and protein function that control networks in cells.

Protein production is a result of a two step process: transcription and translation. First RNA polymerase (RNAP) transcribes DNA into messenger RNA (mRNA) and subsequently a ribosome translates mRNA into a protein. During translation, the protein is in a stable complex with mRNA via the ribosome. At the end of translation, when the ribosome reaches a stop codon, the newly synthesized protein is released from the ribosome as well as the mRNA. Similarly, in transcription, the mRNA stays associated with the DNA via RNAP, and is released when the polymerase reaches a terminal signal.

For translation, the stop codon used are UAA, UGA or UAG. Experimentally one can delete the stop codon function. In one method a piece of DNA is annealed complementary to the sequence along the coding sequence (between start and stop codon). Under such conditions, the translation stalls at the annealing site, and the protein remains in complex with the ribosome and mRNA (Haeuptle, et al. (1986) *Nucleic Acids Res* 14(3):1427–48). In another approach, the stop codon is deleted from the initial DNA. Without stop codon, the ribosome will move along the mRNA to the very last base, but will not release the protein. Such "stopless" coding has been used in experiments where a stable attachment of protein to the mRNA is required, for example, in vitro protein evolution (He et al. (1997) *Nucleic Acids Res.* 25(24):5132–5134) and co-translational protein folding (Fedorov et al. (1995) *Proc. Natl. Acad. Sci. USA* 92(4):1227–1231; Makeyev, et al. (1996) *FEBS Lett* 378(2):166–170).

Normally the signal to terminate transcription is a terminator sequence on the DNA. The signal, in vitro, can also be the very end of a linear DNA. This end-of-DNA termination signal is commonly used in run-off transcription, where RNAP runs to the end of DNA and falls off from it. There are methods to prevent RNAP from reaching the termination signal, for example, by covalently crosslinking the DNA duplex structure (Shi, et al. (1988) *J. Biol. Chem.* 263(1):527–534; Shi, et al. (1988) *J. Mol. Biol.* 199(2):277–293), or by DNA lesion (Sauerbier et al. (1978) *Annu. Rev. Genet.* 12:329–363; Mellon et al. (1989) *Nature* 342(6245):95–98; (Selby et al. (1993) *Science* 263(1):527–534). Under these conditions, mRNA remains attached to the DNA via RNAP.

The human genome is the genetic material in human egg and sperm cells which contain $3 \times 10^9$ base pairs (bp) of DNA. The sequence of $3 \times 10^9$ bp corresponds to 750 megabytes of information. If the sequence of the human genome could be determined, it would be possible to store and manipulate it on a personal computer. Olson (1993) Proc. Natl. Acad. Sci. USA 90:4338–4344. Refinements in experimental protocols, instrumentation and project management have made it practical to acquire sequence data on an enlarged scale. Id. Once genomic sequences are known any gene construct is easy to implement. Once function is understood it becomes possible to realize in vitro protein networks (Jermutus et al. (1998) Curr. Op. Biotechnology 9:534–548) similar to the biological ones.

Arrays offer a systematic way to survey DNA and RNA variation. Lander (1999) Perspective:Nature Genetics, suppl: 1–8. Arrays offer opportunities to analyze large numbers of sequence interactions. Southern et al. (1999) Nature Genetics (supp) 21:5–9. Array-based methods of observing DNA hybridization to complementary RNA are known in the art. Id.

SUMMARY OF THE INVENTION

The present invention is directed to the use of micron scale heaters for gene expression. The present invention is based on the unique determination that in vitro temperature controlled protein expression is achievable on a micron scale.

The micron scale heaters and methods of the present invention are useful for preparing in vitro programmable protein networks and protein micro arrays. In accordance with the present invention protein micro arrays are synonymous with biological chips or DNA chips. The products and methods of the present invention are particularly useful for comparative expression analysis, the analysis of molecular interactions and for providing insights into complex biochemical networks.

One embodiment of the present invention provides an apparatus for controlling gene expression comprising a temperature-controlled template having a nucleic acid construct immobilized thereon. The temperature-controlled template comprises a metal oxide pad with attached electrodes. In a preferred embodiment the metal oxide pad is an indium tin oxide (ITO) pad.

The metal oxide pad is affixed to a substrate, such as glass, for example. The metal oxide pads contain avidin-coated beads, which bind to biotinylated nucleic acid constructs. The metal oxide-substrate combination of the present invention is mounted on a water-cooled brass sample plate. The apparatus also optionally includes a means for detecting protein expression.

Another embodiment of the present invention provides an in vitro programmable protein micro array. Such array includes a plurality of temperature-controlled metal oxide pads (e.g. ITO pads) mounted on a substrate (e.g. glass) wherein each pad is individually temperature-controlled. Each temperature-controlled metal oxide pad comprises at least one immobilized nucleic acid construct of a specific type which is capable expressing a protein which is localized with the nucleic acid construct.

In another embodiment, the present invention provides an in vitro programmable protein network having a plurality of temperature-controlled metal oxide pads (e.g. ITO) mounted on a substrate (e.g. glass) wherein each pad is individually temperature-controlled. Each temperature-controlled metal oxide pad comprises at least one immobilized nucleic acid construct of a different type which is capable expressing a protein which is released from the nucleic acid construct.

The present invention also provides an in vitro method of controlling gene expression by immobilizing a nucleic acid construct on a temperature-controlled template, applying a cell extract, expressing a protein and detecting the expression of the protein.

DETAILED DESCRIPTION OF THE INVENTION

The present invention is directed to an apparatus and method of controlling the expression of anchored genes.

Specifically, it has been discovered by the present inventors that anchoring gene constructs on a local temperature heater and using cell extracts as the reaction medium, permits controlled protein synthesis. In accordance with the present invention, it has also been found that by using different nucleic acid constructs, the expressed protein remains bound to the DNA coding sequence or is released from it. When the protein remains bound to the DNA coding sequence, protein chips are obtained.

An in vitro programmable protein micro array is therefore provided having a plurality of temperature-controlled metal oxide pads 102 mounted on a substrate 104 wherein each pad is individually temperature-controlled. The temperature-controlled metal oxide pads have at least one immobilized nucleic acid construct 106 thereon. The immobilized nucleic acid construct on the micro-array is uniform. By "uniform" is meant one specific type of nucleic acid construct (e.g. DNA encoding luciferase or polymerase) which is capable of expressing a protein. In accordance with the present invention, the expressed protein is localized with the immobilized nucleic acid construct as a consequence of the deletion of the stop codon from the nucleic acid construct.

The present invention also provides an in vitro programmable protein network having a plurality of temperature-controlled metal oxide pads mounted on a substrate wherein each pad is individually temperature-controlled. The temperature-controlled metal oxide pads have at least one immobilized nucleic acid construct thereon. The immobilized nucleic acid construct on the programmable protein network is non-uniform. By "non-uniform" is meant a plurality of diverse nucleic acid constructs (e.g. DNA encoding each molecule in a complex biochemical pathway, such as a gene regulation pathway (see Example 5, infra) which are each capable of expressing a protein. The skilled artisan appreciates, in accordance with the present invention, that two or more non-uniform nucleic acid constructs may be applied to two or more adjacent temperature-controlled pads to cause sequential protein expression. By "adjacent" is meant temperature-controlled pads that are less than about 2 mm apart, so as to permit migration of protein from one pad to another, by diffusion, for example.

In accordance with the present invention, the expressed protein of the protein network is released from the immobilized nuclei acid construct and migrates to an adjacent pad (containing a construct encoding the next protein in the pathway) where additional and diverse protein is controllably expressed. Release of the protein is achieved in accordance with the present invention by preparing a nucleic acid construct which contains a stop codon within the coding region of the construct.

Accordingly, the present invention employs an apparatus containing nucleic acid constructs immobilized at designated positions thereto and methods that are useful for the controlled expression of proteins for the manufacture of programmable protein networks, protein micro-arrays. The present invention also provides individual chips for comparative expression analyses.

By "nucleic acid construct" is meant a DNA having three regions: a control region, a protein coding sequence, and a spacer. A preferred control region comprises a T7 promoter. Another preferred control region comprises a T3 promoter. A preferred spacer comprises at least about 30 base pairs. The present invention contemplates a spacer region having several hundred base pairs.

"A temperature-controlled template" as used herein, refers to at least one individual metal oxide pad fabricated on a rigid substrate, such as for example a gold-coated glass or silicon substrate. Preferred metal oxide pads of the present invention include indium tin oxide (ITO) pads. Preferably, the ITO pads are about 1 $\mu$m thick and have an area of about 100 $\mu$m×100 $\mu$m, more preferably about 20 $\mu$m×20 $\mu$m and most preferably about 10 $\mu$m×10 $\mu$m. A preferred substrate is glass. The preferred device comprises one or more ITO pads fabricated on a glass substrate.

In accordance with the present invention temperature is used as a control parameter. Local variation of temperature is achieved by applying electrical current to the individual pads.

The present invention provides an ITO-micro-heater pad fabricated on a glass coverslip. Any number of micro-heater pads are contemplated by the present invention to be fabricated on a glass coverslip based on the surface area of the glass coverslip and the surface area of the micro-heater pad. Moreover, it is contemplated that each micro-heater pad will contain either one type of DNA, allowing for the formation of a protein chip or several different types of DNA, allowing for the formation of protein networks.

In accordance with the present invention, each ITO pad acts as an individual heating element to provide a local temperature control of gene expression. Each ITO pad is connected to a power source, preferably by gold electrodes 108. In a preferred embodiment the ITO pads are spaced about 1 um to about 5 mm apart. More preferably the ITO pads are spaced about 1 mm apart.

The temperature of individual ITO pads is controlled by a conventional power source. The pads are controlled to cover a temperature range from about 1° C. to about 100° C. and most preferably from about 5° C. to about 40° C. The resistance of the pads is preferably about 5 Ohms to about 100 Ohms and most preferably about 50 Ohms. To heat the pad, a dc current from 0 to about 100 mA is applied. Most preferably the applied dc current is about 40 mA.

In one embodiment of the present invention, DNA is attached to its encoded protein by the alteration of transcription and translation. In accordance with the present invention a double alteration method is used to prevent both transcription and translation termination.

To prevent transcription termination, avidin is attached to the terminal end of biotinylated DNA and RNAP moves toward the biotin end. The translation termination is prevented in accordance with the present invention by deletion of the stop codon from the initial DNA. Without a stop codon, the ribosome does not release the protein. Biotin modified nucleic acid (gene) constructs are coupled to avidin coated beads which are immobilized at designated positions on the metal oxide substrate. Prevention of transcription and translation termination results in a final structure that consists of mRNA linked to DNA via RNA polymerase and the protein bound to mRNA through the ribosome.

In accordance with the present invention a Wheat Germ Coupled T7 Transcription and Translation kit (Promega, Madison, Wis.) is used as the reaction medium to transcribe and translate the immobilized genes. However, the skilled artisan appreciates that the reaction medium may be conventionally varied depending upon the desired protein. The concentration of the protein product translated is about $10^8$ molecules (encoded from $-10^6$ immobilized DNA constructs). The linear DNA constructs (T7 promoter sequence, gene sequence and linker) are designed so that the synthesized protein is either attached or released from its DNA coding sequence. Shumo Liu, et al. (1999) "Towards a Protein Micro-array: Binding a Protein to its DNA and mRNA" (submitted to Biotechniques for publication).

In accordance with the present invention it has been found that gene function, e.g. protein synthesis is controllable in a current/temperature-dependent manner. Increasing the dc current supplied to the electrodes leads to a concomitant temperature increase resulting in a rapid increase in detectable protein synthesis within about 10 seconds. Protein synthesis is detectable with an optical lens 116 using a photo multiplier tube 118. However, the skilled artisan can readily detect protein synthesis by other means as are conventionally understood. When the temperature of at least one individual pad is increased, detectable protein expression is turned on. When the temperature is lowered, protein expression decreases. When no heat is applied, detectable protein expression stops. Thus, the present invention provides a method for sequentially controlling the temperature of the metal oxide pads and the concomitant expression of protein in an on/off manner.

In accordance with the present invention, when the reaction medium is maintained at low temperature (5° C.), all the reactions in the cell extract are turned off. When the metal oxide pad-substrate is mounted on a water-cooled 110 brass sample plate 112 maintained at 5° C., a homogeneous temperature of 5° C. is imposed for the reaction medium by cooling the sample from the top, using a thermal anchored cover slide 114. In accordance with the present invention, the temperature of individual metal oxide pads is controlled to cover a temperature range from about 5° C. to about 40° C. Thus, genes can function at desirable rates depending on the applied local temperature.

Another embodiment of the present invention provides an in vitro programmable protein micro-array having immobilized DNA on a temperature controlled template. By "programmable" is meant electronically controlled protein expression on an individually heated pad. A programmable protein micro-array of the present invention is contemplated to express a desired type of protein in detectable quantities for comparative expression analyses. The expressed protein of the micro-array is bound to mRNA through the ribosome and is therefore localized with its DNA.

Still another embodiment of the present invention provides an in vitro programmable protein network. In accordance with the present invention a multiplicity of diverse DNAs encoding a series of proteins or an entire biochemical pathway are immobilized to individual ITO pads between electrodes. By controlling the flow of electricity to each individual pad in sequence, detectable quantities of protein are expressed and released in sequence. Thus, the controlled expression and release of a first protein in a pathway migrates to an adjacent pad containing the DNA encoding the next protein in the pathway, which is then controllably expressed leading to the ultimate synthesis of a desired end product.

This invention is further illustrated by the following examples, which are not to be construed in any way as imposing limitations upon the scope thereof. The terms and expressions which have been employed in the present disclosure are used as terms of description and not of limitation, and there is no intention in the use of such terms and expressions of excluding any equivalents of the features shown and described or portions thereof. It is to be understood that various modifications are possible within the scope of the invention. All the publications mentioned in the present disclosure are incorporated herein by reference.

The following examples are illustrative of temperature controlled expression of the North American firefly Luciferase (luc) gene. The Luciferase gene is useful to assay because of its fast folding time and also because it is one of the most sensitive measures of protein expression levels. Luciferase catalyzes light emission in the presence of luciferin and some other chemical factors. It can thus be rapidly detected by its luminescence. Wilson T et al. (1998) "Bioluminescence" Ann. Rev. Cell Devel. Biol. 14: 197–230.

EXAMPLE 1

ITO Heating Pads

Figure 1:
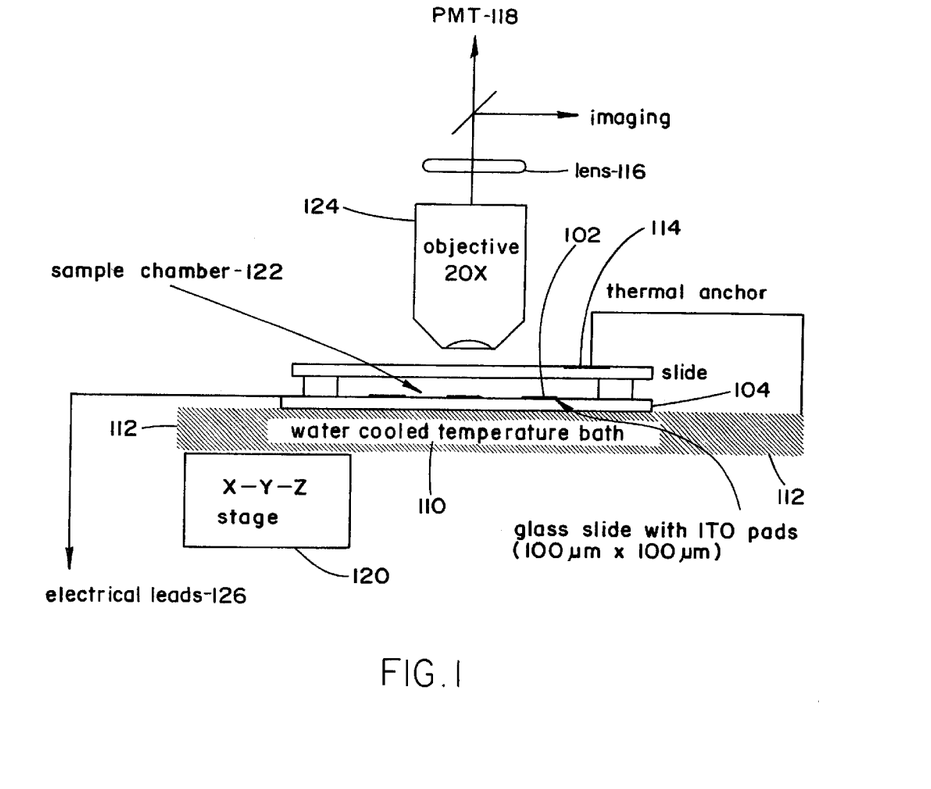
FIG. 1 is a schematic of the experimental setup. The ITO glass slide is mounted on a water-cooled bath. The sample chamber is thermally anchored to define a homogeneous sample temperature. A simple reflection microscope is used to visualize and detect using a PMT detector. (a) (inset): Photo of the ITO slide. 6 transparent ITO pads (100 $\mu$m×100 $\mu$m) are connected with the gold electrodes. (b) Photo of a single ITO pad after lithographic patterning of avidin coated beads to immobilize the biotin-DNA construct. (c) Schematic of DNA attachment and in-vitro transcription/translation.
Figure 1A:
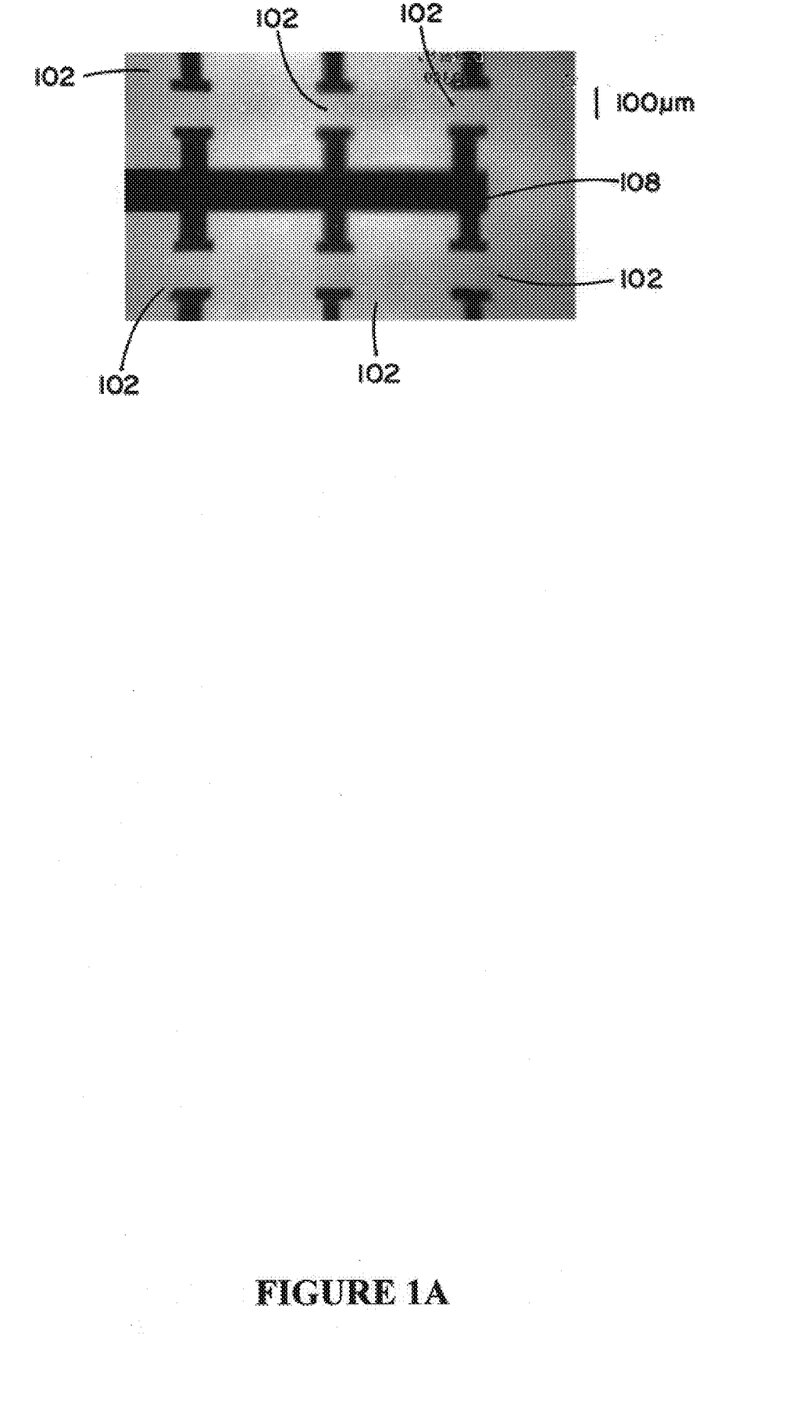
Figure 1B:
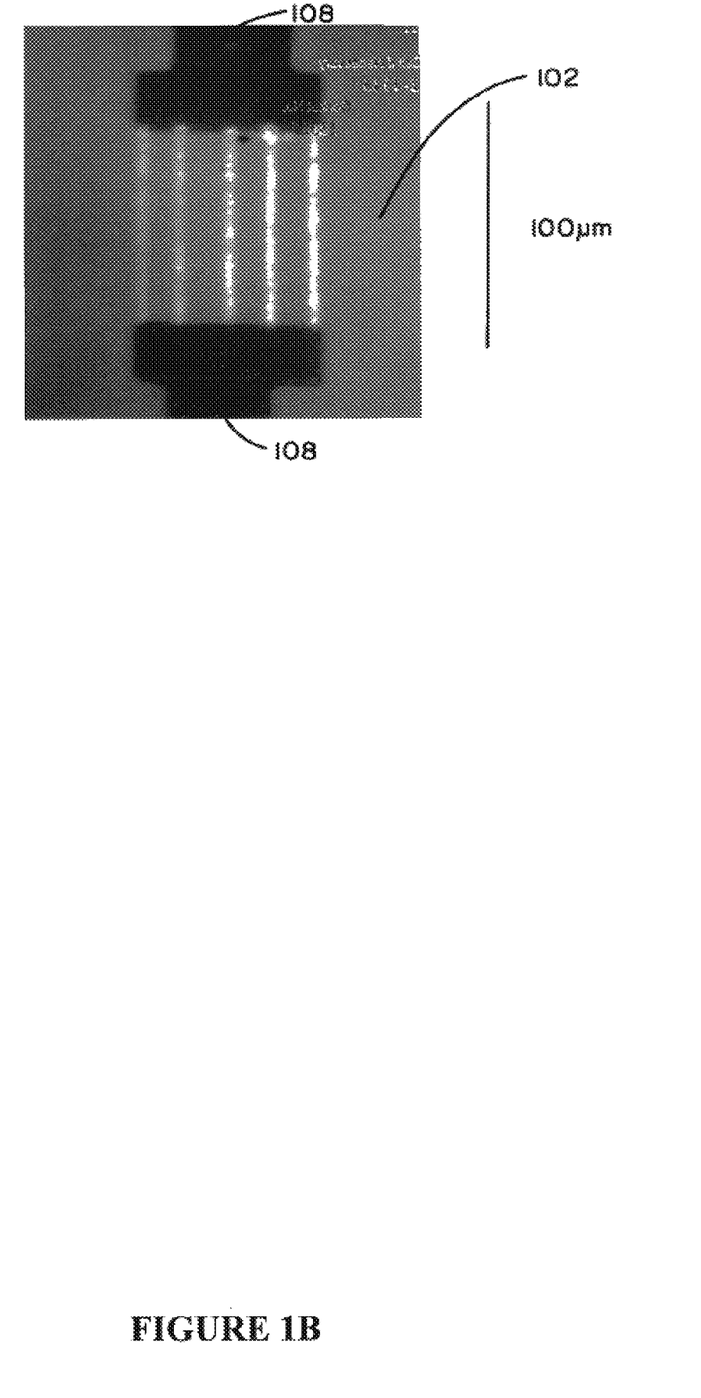
Figure 1C:
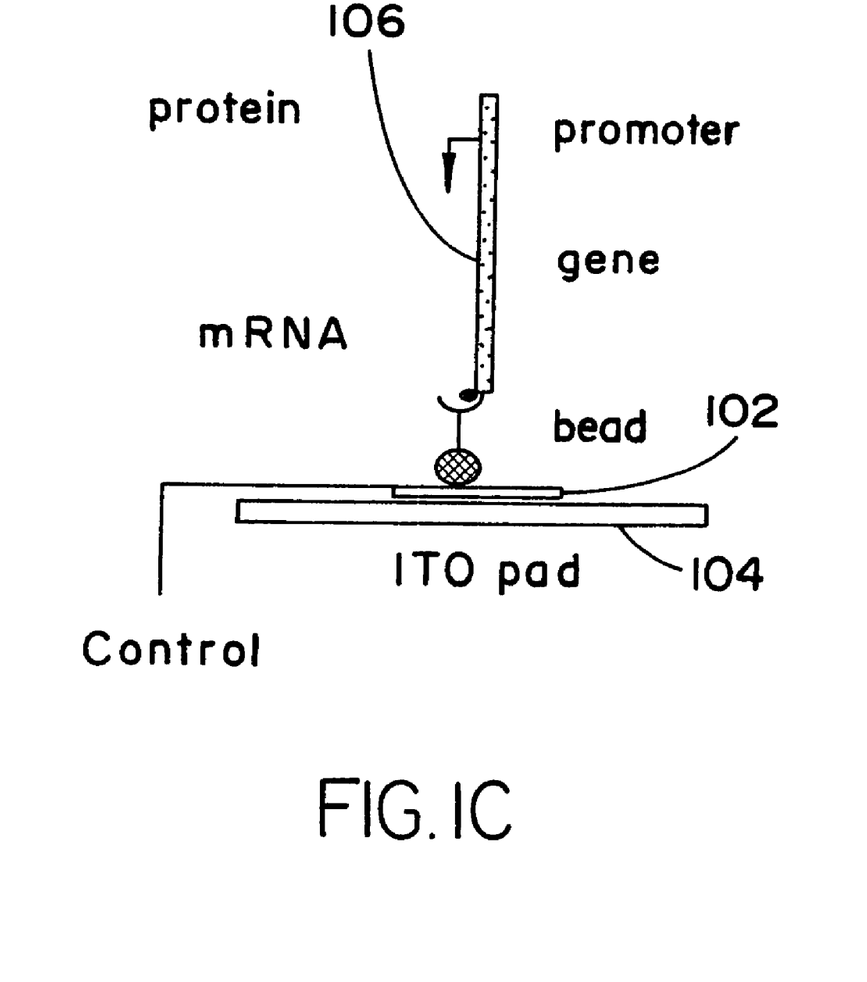
Figure 2A:
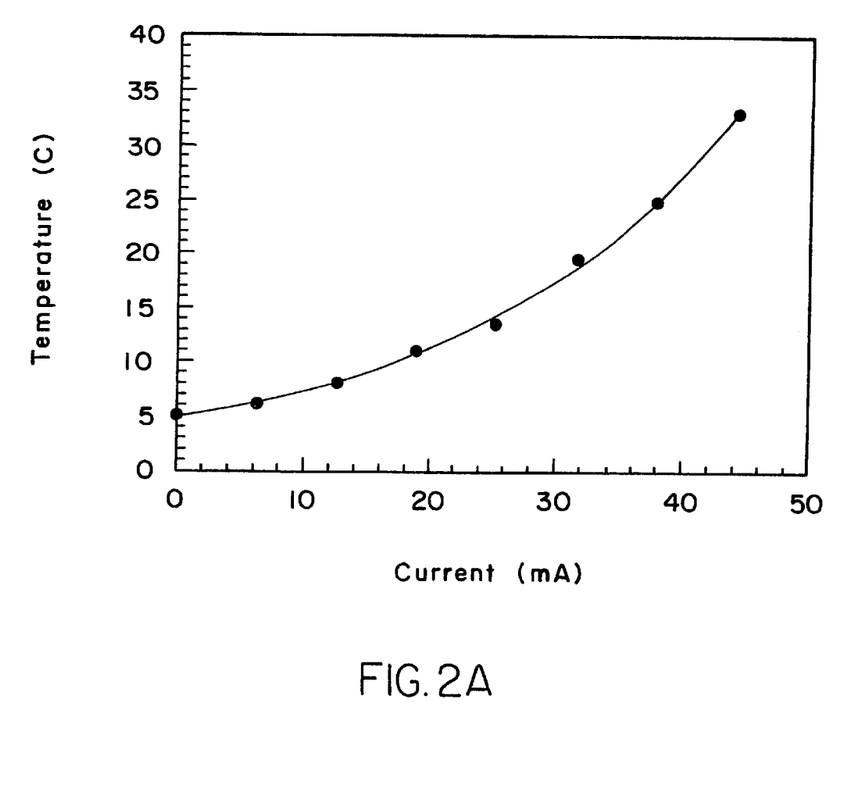
FIG. 2A: A calibrated thermocouple is put in contact with the ITO pad. Temperature versus current is plotted. The solid line is an exponential fit.
Figure 2B:
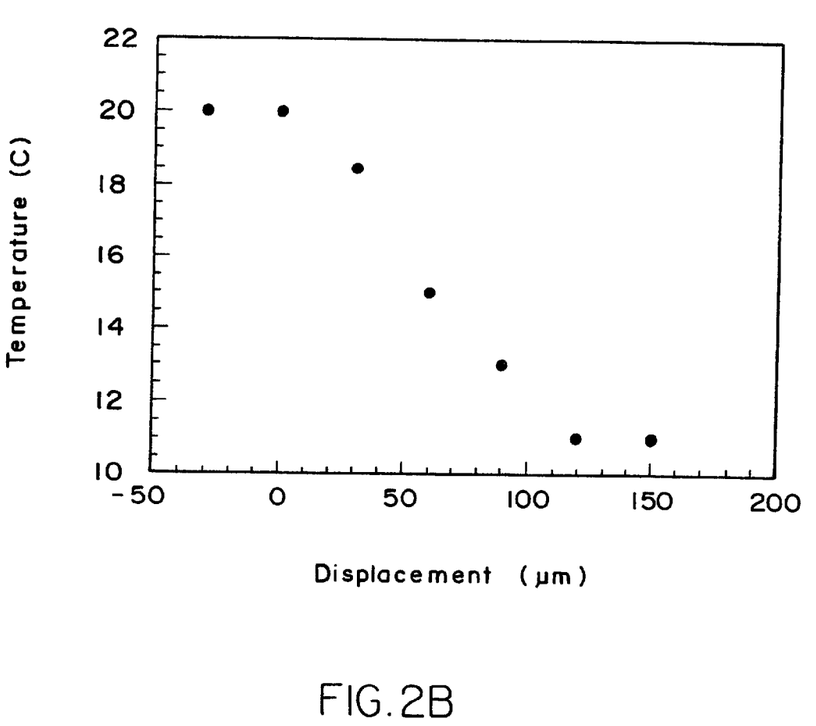
FIG. 2B: Temperature profile recorded by scanning the thermocouple along to the ITO pad.

A picture of the protein chip substrate is shown in FIG. 1*a* with 6 ITO pads and their electrical connections. Each ITO pad (100 $\mu$m×100 $\mu$m connected by gold electrodes) acted as an individual heating element (inset 1*b*). The resistance of the pads was 50 Ohms. To heat the pad, a dc current 126 (HP 3630) from of 0 to 40 mA was applied. Power dissipation was 80 mW for a maximum current of 40 mA. The temperature of the ITO pad as a function of applied current is plotted in FIG. 2A. It was measured with a calibrated thermocouple (Omega: CHCO-001) positioned in contact with the ITO pad using a XYZ translation stage 120. FIG. 2b shows the temperature profile of the heating pad as a function of distance. The pad was heated to 20° C. and the temperature profile clearly shows that the temperature of the pad decays over a length scale comparable to the pad size. The ITO glass was mounted on a water-cooled brass sample plate maintained at 5° C. In order to impose a homogeneous temperature of 5° C. for the reaction medium the sample was cooled from the top as well, using a thermal anchored cover slide (see FIG. 1).

EXAMPLE 2

A: Construction of Biotin Modified DNA Coding Sequences

The nucleic acid construct has three regions: the control region, the luciferase sequence (1.65 lb), and a spacer. The control region has a T7 promoter sequence for transcription by T7 RNAP. In one nucleic acid construct the stop codon of the luciferase sequence was deleted by PCR using luc C-terminal primer (lucC). Immediately downstream of luc was a spacer sequence. Since several codons on mRNA were covered by RNAP and about 30 amino acid residues were wrapped inside the ribosome tunnel, about 40 or more codons were needed downstream of luc. Accordingly, a spacer of 717 base pairs was added (the spacer sequence originated from gfp, green fluorescent protein). The entire coding sequence gave one messenger the luc-spacer fusion protein without stop codon.

DNA fragments were first made by PCR. These fragments were joined together by directional ligation, followed by PCR of the joined sequence. The ligated DNA was further amplified by PCR. For immobilization on avidin coated beads, the C-terminal primer (at the end of the transcription) was biotinylated. Shumo Liu, et al. (1999) "Towards a Protein Micro-array: Binding a Protein to its DNA and mRNA" (submitted to *Biotechniques J.* for publication)

B: DNA Biotinylation and Immobilization on Beads

Biotin was attached to the 5' end of a desired DNA primer using a biotinylation kit (Amersham-Pharmacia Biotech, Piscataway, N.J.) and purified by G-25 gel filtration column (AmiKa, Columbia, Md.). Using one biotinylated primer, the PCR product was biotinylated at the end corresponding to the primer site. NeutrAvidin (a variation of avidin) coated polystyrene beads (1 μm diameter, 3.6×10$^7$ beads/μl, 24 pmol/μl of biotin binding capacity, Molecular Probes, Eugene, Oreg.) were the solid medium for DNA immobilization. Biotin binds strongly to avidin with a dissociation time scale on the order of about a month. The biotin-binding site of avidin is in a cavity bout 9A below the avidin molecule surface. The beads were washed in TBSM (TBSM: 10 mM Tris-Cl, pH 8.0, 50 mM NaCl, 5 mM MgCl$_2$) once and suspended in TBSM (diluted 10 times compared to the original bead product package). DNA (0.1 pmol/μl) and the resuspended beads were mixed at 1:1 ratio, the binding was at 37° C. for 30 min., or at room temperature (23° C.) for several hours. Before using the beads for the next reaction, they were collected by centrifugation at 14,000 g for 5 minutes.

C: PCR

The PCR buffer was similar to that for RapidCycler (Idaho Technology, Boise, Id.); it had 200 mM Tris-Cl, pH8.4, 2.5 mM MgCl$_2$ and 0.2 mM of each of the four dNTP's. The reaction has 0.25 μM of each of the primers (P1: 5' GATTACGCCAAGCTCTAATACGACTCACTATA 3' (SEQ ID NO:1); lucC 5' CACGGCGATCTTTCCGC-CCTTCTTG 3' (SEQ ID NO:2); P2 5' TTTGTATAGT-TCATCCATGCC 3' (SEQ ID NO:3)) and less than 2 nM of the starting template. Either Advantage 2 (Clontech, Palo Alto, Calif.) or a 1/32 mixture of pfu (Promega) and Taq (Life Technologies, Rockville, Md.) was used. The reaction volume was 30 μl in a 0.2 ml thin-wall tube on a thermal cycler, Hybaid Sprint (Hybaid, UK), in a tube simulated temperature control mode of the cycler. The thermal cycler parameters were 94° C. for 1 second, the lower temperature of the two primer Tm's (melting temperatures) for 1 second and 74° C. for a duration of 1 second per 50 base pairs of the template length. Total cycles were 25 to 30 cycles. PCR product was treated at 25° C. for 15 minutes with 1 unit of Klenow Fragment of *E. coli* DNA polymerase I (New England Biolabs, Beverly, Mass.). It was then purified with a PCR purification kit (Amersham-Pharmacia Biotech) and eluted and stored in 50 μl Tlow E (TlowE: 10 nM Tris-Cl, pH 8.5, 0.1 mM EDTA). The quality of PCR was examined by agarose gel electrophoresis. If multiple DNA bands appeared on the gel, the band of correct length was excised and the DNA extracted with a DNA extraction kit (Qiagen, Valencia, Calif.).

D: Ligation

Two DNA fragments, blunt-ended and PCR made, were joined together by ligation. One fragment is biotinylated at one end and immobilized on NeutrAvidin coated polystyrene beads via biotin-avidin binding. The other end was free and not phosphorylated. The second fragment was free in solution and was phosphorylated at one end, the end for ligation. Ligation reactions joined the free end of the immobilized DNA fragment to the phosphorylated end of the free fragment. Ligation reaction solution had 1 pmol of immobilized fragment, 0.1 pmol of free fragment, 2.5 μl of clonable ligation mix (Novagen, Madison, Wis.) and 5 μl of H$_2$O. The reaction was performed at room temperature and lasted 15 minutes. The beads were collected by centrifugation, at 14,000 g for 5 minutes. The supernatant was discarded and the beads resuspended and stored in 10 μl of TE (TE:10 mM Tris-Cl, pH 8.5, 1 mM EDTA).

EXAMPLE 3

To immobilize the NeutrAvidin-coated polystyrene beads at precise positions a technique previously described was employed. Shivashankar et al. (1998) *Appl. Phys. Lett.* 73:417–419. A thin gold film (30A) was sputtered on the ITO slide to be used as an absorption surface. An infrared laser beam was focused to a diffraction spot at the gold film, heating surface for a short time. Avidin covered beads (1 μm, Molecular probes) were immobilized on the ITO pad during laser absorption. As the laser was moved, lithographic-like patterns were written (FIG. 1, inset b). The avidin beads were absorbed onto the surface along the infrared beam trajectory. A typical number of beads absorbed was 10$^4$ for the lithographic pattern shown in FIG. 1, inset a. Thus, for each ITO pad, given 100 DNA constructs per bead, the total number of DNA was about 10$^6$. Biotinylated DNA sequences (2 μl, concentration 0.1 picoM) were incubated on the ITO lithographic pattern at 30° C. for 1 hour after which the sample was washed to remove unbound DNA sequences. The volume of the sample cell was 25 μl. The DNA molecules immobilized on beads were then subjected to in vitro coupled transcription and translation.

A kit (Wheat Germ Coupled/T7 Transcription and Translation, Promega, Madison, Wis.) was used for in vitro transcription and translation of the luciferase gene and the spacer sequence. The total reaction volume, 50 μl, contained about 0.3 pmol of bead-immobilized DNA. The reaction was carried out at 25° C. for 50 minutes, with occasional shaking to keep the beads in suspension.

The total of 50 µl of reaction product was separated into supernatant with DNA attached beads and supernatant. After a brief centrifugation, 20 µl of supernatant was collected, and the bead pellet was mixed with another 20 µl of supernatant. This portion of the reaction product was assayed for luciferase activity.

Luciferase reaction mix (Promega), which contained 0.8 mM luciferin and stabilizing agents, was mixed with the transcription and translation sample. Light emission from the reaction was measured with a Beacon 2000 (PanVera, Madison Wis.) adapted so that the excitation light was blocked, and the emission filter omitted. The sample chamber 122 cover on the instrument was modified to allow injection of samples into the reaction tube. In the sample chamber, 80 µl of luciferase reaction mix was set at 25° C. 20 µl of transcription and translation product was then injected into the luciferase reaction. Luminescence measurement sampling rate was about 7 seconds. The total light intensity, in RLU (relative light units), was collected by an NEC PC computer and plotted with KaleidaGraph software on an Apple G3 computer. The instrument has a minimum threshold of about 0.01 RLU.

It is known that luciferase fused with a peptide at the C-terminal end is functional (Makeyev, Kolb, et al. 1996). The functionality of the luciferase construct was confirmed by measuring the light output. For luminescence detection a simple microscope with a 20 X objective lens 124 was used to visualize the ITO pads and a PMT (Hamamatsu) was employed to detect luminescence. The calculated light collection efficiency was 0.75%, for the numerical aperture of the lens used and the quantum efficiency of the detector at the working wavelength. Thus, for every 1000 photons emitted 7.5 photons were detected. The light output was 2 RLU (relative light units), where the threshold level for the instrument was 0.01 RLU. The light emission demonstrates that fusion luciferase is functional.

Figure 3:
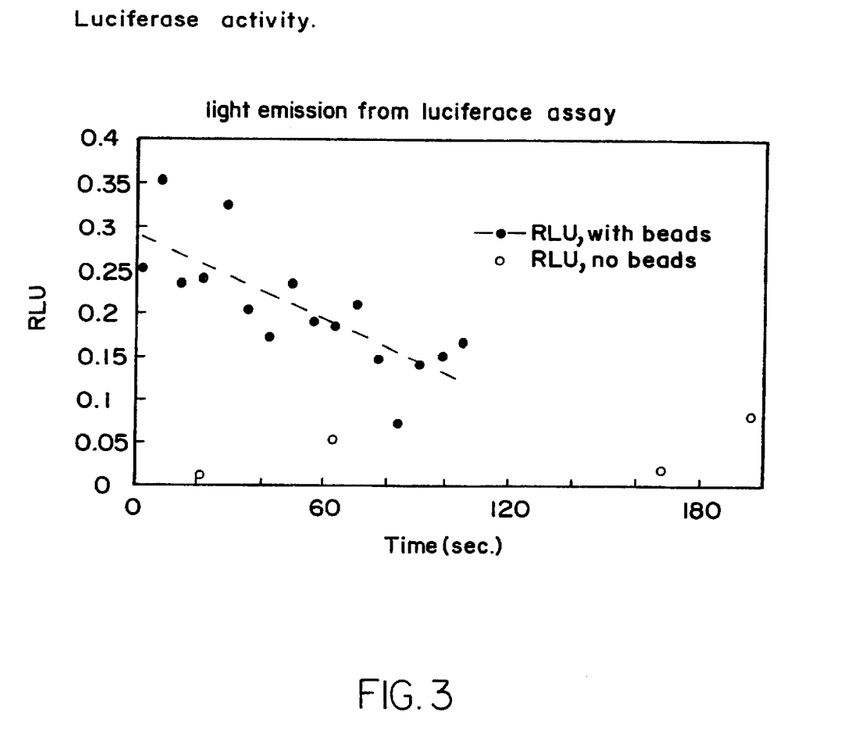
FIG. 3 shows the light emission of luciferase plotted as a function of time.

To determine if the luciferase made from the immobilized DNA was in the supernatant or stayed associated with the DNA coated beads, the supernatant was assayed for luciferase activity. After washing the supernatant, 25 µl of luciferase assay reagent (Promega) was added. The intensity profile of the ITO pad showed strong activity on the ITO pad exclusively. The light emission registered was near the instrument noise level and 26 out of 30 measurements were below the detection threshold (FIG. 3). Therefore, light emission and thus the protein was localized with the beads, not with the supernatant.

EXAMPLE 4

Figure 4:
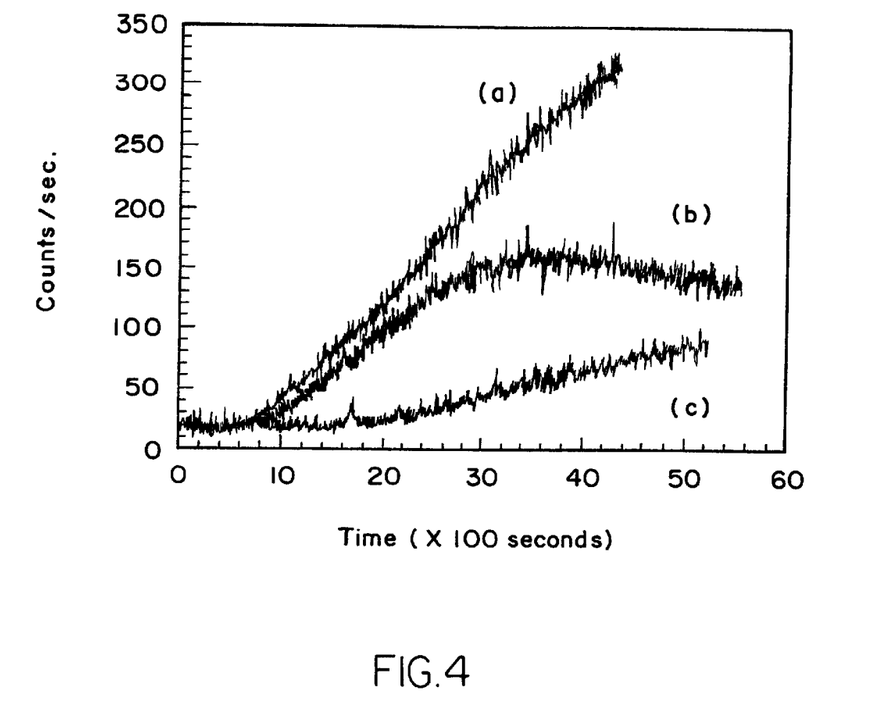
FIG. 4 shows measured luminescence at T=30° C. versus time for the three DNA constructs immobilized on the ITO slide. (a) the mRNA and Protein are released; (b) mRNA is bound to the DNA but the protein is released; (c) both the mRNA and the protein are bound to the DNA construct.

In FIG. 4 the time scale of luciferase synthesis for three different gene constructs is plotted at T=30° C. In one construct the mRNA and the protein were released. In the second one mRNA was bound to its DNA but the protein was released. In the last one both mRNA and protein stayed bound to their DNA. The reaction was most efficient when mRNA and protein are released (FIG. 4a). Under similar reaction conditions the efficiency was reduced when the mRNA was bound, and even further reduced when mRNA and the protein were bound (FIGS. 4b&c). The onset of detectable protein synthesis was determined to occur at about 15 minutes. Those results were consistent with studies of in-vitro transcriptions and translation of luciferase gene. (Kolb et al. (1994) EMBO J.13:3631–3637; Makeyev et al. (1996) FEBS Lett. 378:166–170; Yang et al. (1997) FEBS Lett. 417:329–332.)

Figure 5:
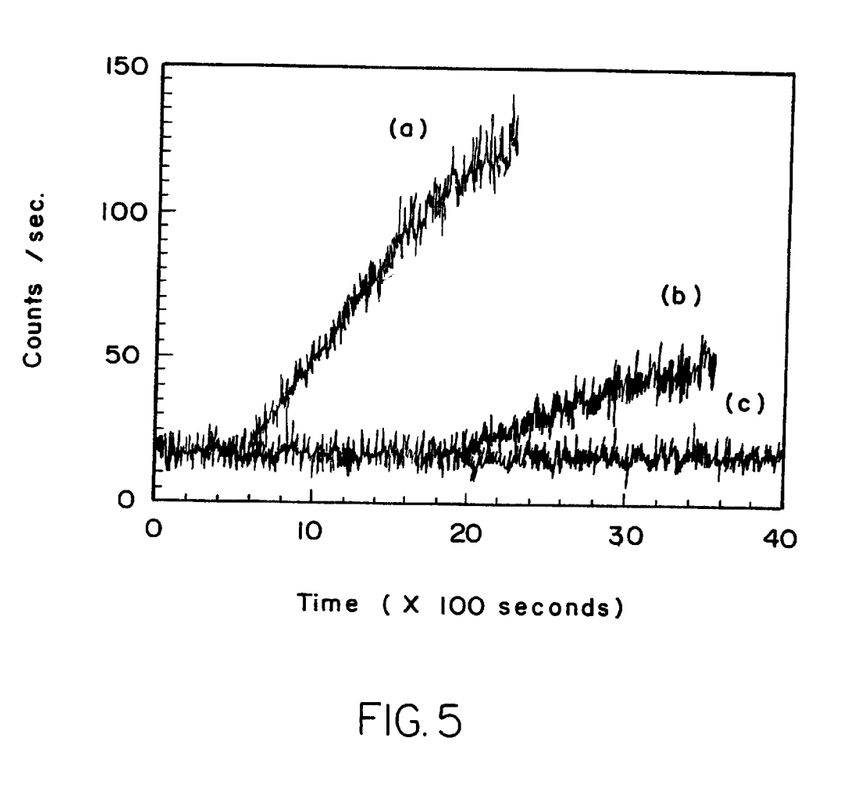
FIG. 5 shows controlled expression of Luciferase on the ITO slide. Three independent measurements of luminescence verus time at different temperatures: (a) T=5° C.; (b) T=18° C.; (c) T=28° C.

FIG. 5 demonstrates the attachment of mRNA. Luciferase activity was observed after about 30 minutes. At T=28° C. a further enhancement of the synthesis was recorded with a detectable onset after about 15 minutes (FIG. 5a).

To further test the control and localization of gene expression, DNA constructs were immobilized on two neighboring ITO pads. This test employed the construct where mRNA and protein were bound after transcription and translation. Controlled expression was carried out on one of the ITO pads by applying a current I=40 mA (T=28° C.) for 30 minutes while maintaining the water bath at 5° C. The sample cell was then washed and 25 µl of luciferase assay reagent (Promega) is added. Intensity profile of the ITO pad (FIG. 6) was recorded by displacing the sample mounted on the XYZ stage. Similar data was recorded on the second ITO pad kept at the bath temperature of 5° C. with no observed activity. The data shows controlled expression and localization of the produced protein at the surface of the ITO pad when heated.

Figure 6:
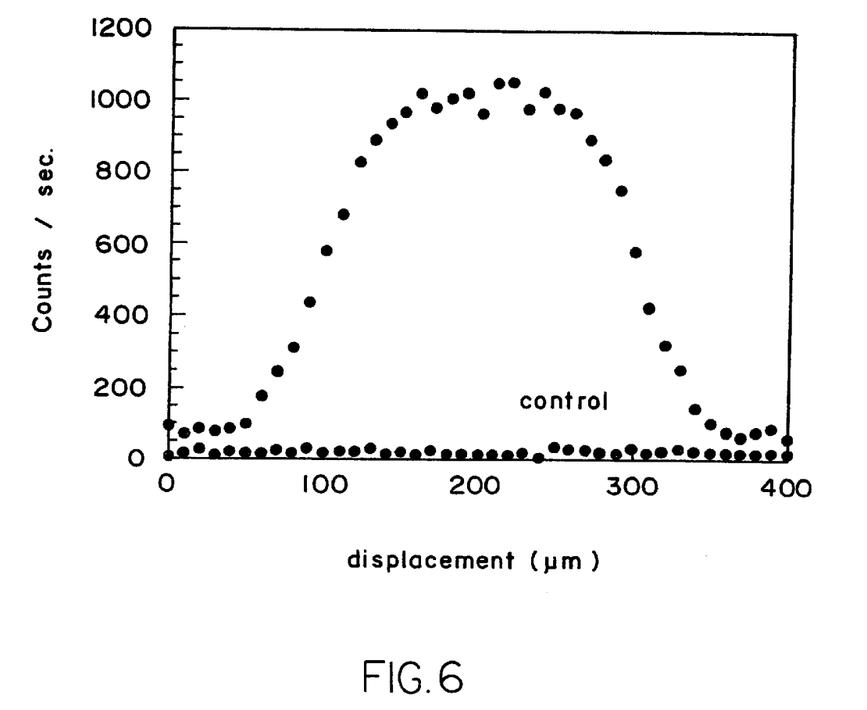
FIG. 6 shows a line scan of controlled expression on the ITO slide. The Luciferase protein is attached to RNA and DNA after translation. The Intensity profile of the ITO pad shows localization of the protein. The control shows the Intensity profile of a second pad, which is not heated.
Figure 7:
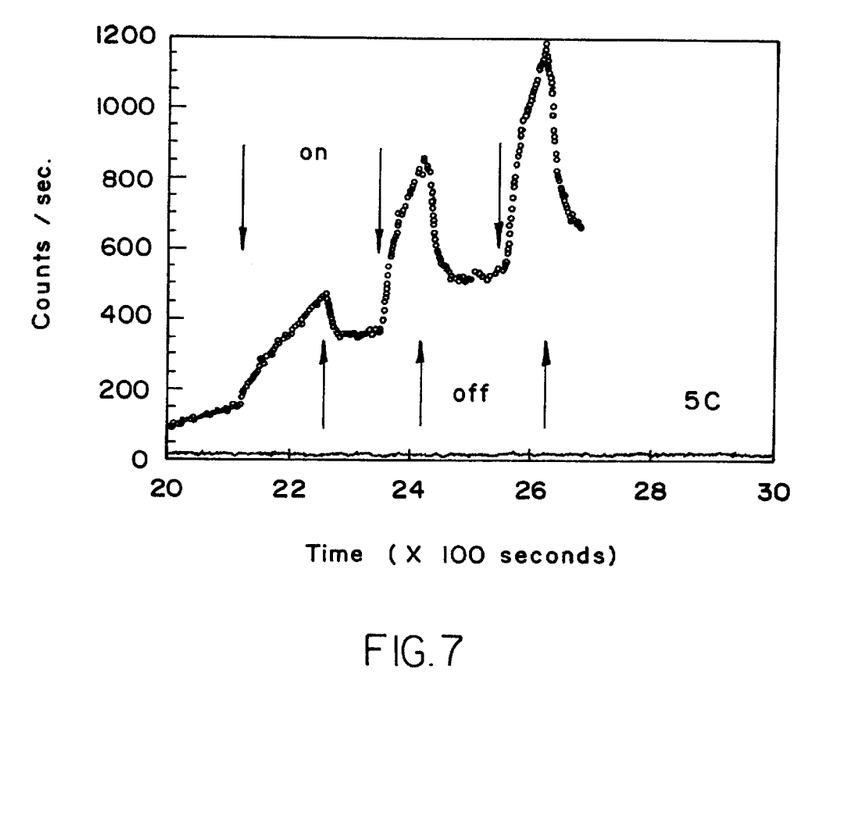
FIG. 7 demonstrates protein production observed by luminescence as the ITO pad current is turned on at 40 mA and off. The bottom recording indicates luminescence when the construct is not anchored to the ITO but the entire reaction medium is present.

The catalytic activity of luciferase luminescence was used to obtain a time constant for the ITO heater pad. In FIG. 6 the luciferase activity is plotted as a function of time. The activity was monitored during the in vitro reaction. A detectable concentration of the protein was achieved with the water bath at 5° C. Turning on the current (T=30° C.) resulted in a rapid increase in light intensity within about 10 seconds. The steep rise in intensity was due to the increase in catalytic activity of luciferase gene between 5 and 30° C. in about 10 seconds. Thus, the time needed to heat and cool the pad from 5 to 30° C. was about 10 seconds. (FIG. 7) In addition during each temperature cycle, new proteins were synthesized leading to a net increase in luminescence. In the absence of new protein synthesis the temperature dependant catalytic activity of Luciferase was measured.

EXAMPLE 5

Figure 8:
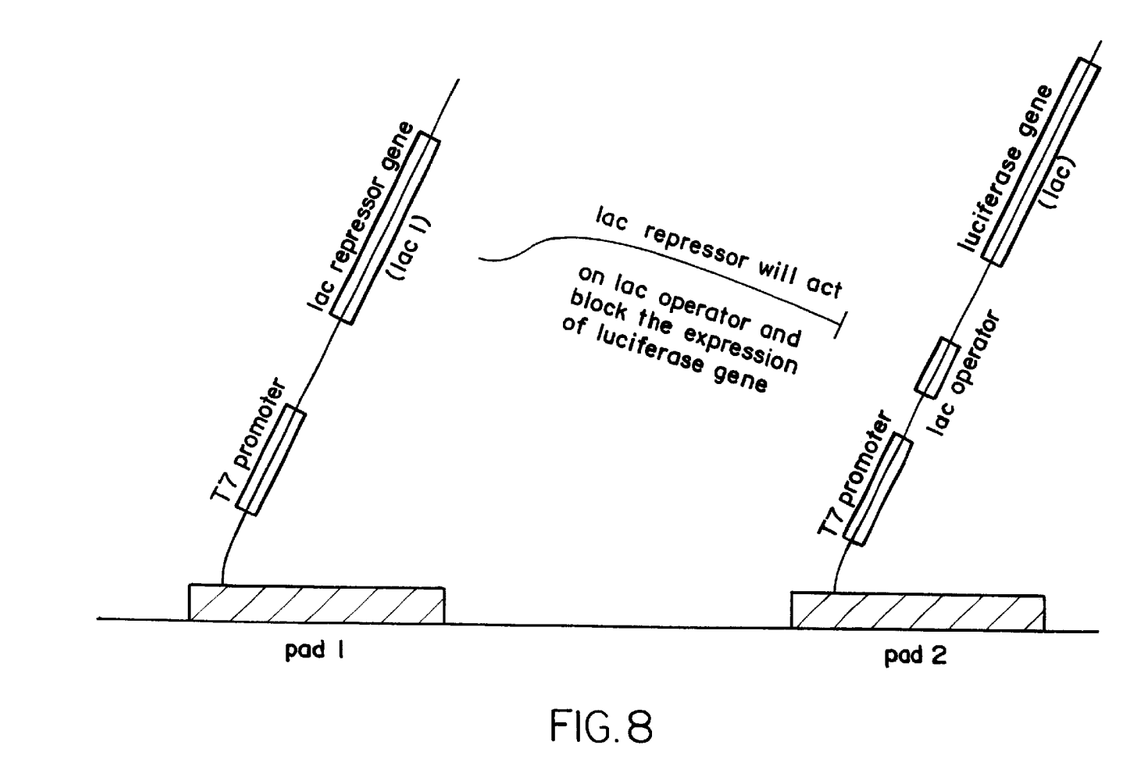
FIG. 8 shows a programmable protein network.

In a programmable protein network of the present invention at least two non-uniform DNA constructs are separately immobilized on at least two separate pads in accordance with the present invention, as shown in FIG. 8. Both constructs comprise a T7 promoter. Pad 2 has the luc (luciferase gene) ligated to the lac operator and is heated to a temperature of 25° C. Pad 1 has the lacI (lac repressor gene of *E. coli*). Temperature is controlled by the experimenter. When pad 1 is heated to 25° C., lacI is expressed and the product of lacI, the lac repressor, is released into the surrounding medium. The lac repressor migrates (by diffusion, for example) to pad 2 and binds to the lac operator, thus blocking the expression of luciferase. Once expression of luciferase is blocked, expression is turned off and pad 2 goes "dark". When pad 1 is maintained at about 5° C., the lacI is not expressed, and the luc on pad 2 is expressed (pad 2 is illuminated or "on").

What is claimed is:

1. An in vitro method of controlling gene expression comprising anchoring at least one nucleic acid construct on a temperature-controlled template, applying a cell extract and expressing at least one protein.

2. The method of claim 1 further comprising detecting the expressed protein.

3. The method of claim 1 wherein said nucleic acid construct comprises a control region, a coding sequence and spacer region.

4. The method of claim 3 wherein said control region comprises a promoter sequence.

5. The method of claim 4 wherein said promoter sequence comprises a T7 promoter.

6. The method of claim 3 wherein said coding sequence comprises a polymerase chain reaction (PCR) deleted stop codon.

7. The method of claim 3 wherein said spacer region comprises at least about 70 base pairs.

8. The method of claim 1 wherein said nucleic acid construct is DNA.

9. The method of claim 8 wherein said DNA construct is C-terminally biotinylated.

10. The method of claim 1 wherein said temperature-controlled template comprises one or more metal oxide pads affixed to a substrate.

11. The method of claim 10, wherein said metal oxide pads further comprise indium tin oxide (ITO).

12. The method of claim 10 wherein said substrate is glass.

13. The method of claim 10 wherein said metal oxide pads contain avidin-coated beads.

14. The method of claim 10 wherein said metal oxide pads comprise about 10 um by about 10 um to about 100 um by about 100 um.

15. The method of claim 10 wherein said template is heated by means of electrodes attached to the metal oxide pad.

16. The method of claim 15 wherein said electrodes conduct an applied dc current.

17. The method of claim 16 wherein said dc current applied is about 1 mA to about 40 mA.

18. The method of claim 15 wherein said template is heated to a temperature which causes an onset of protein expression.

19. The method of claim 18 wherein said protein expression is stopped by reducing the heat applied to said template.

20. The method of claim 10 wherein said metal oxide-substrate is mounted on a water-cooled brass sample plate.

21. The method of claim 20 wherein said water-cooled brass sample plate is maintained at a temperature wherein protein expression is prevented.

22. The method of claim 21 wherein said water-cooled brass sample plate is maintained at about 5° C.

23. The method of claim 1 wherein said template is controlled at a temperature of about 5° C. to about 100° C.

24. The method of claim 10 wherein said metal oxide pads have a resistance of about 50 Ohms.

25. The method of claim 1 wherein said expressed protein is localized with the immobilized nucleic acid.

26. The method of claim 1 wherein said expressed protein is released from the immobilized nucleic acid.

27. An in vitro method of sequentially expressing proteins comprising anchoring a first nucleic acid construct on a first temperature-controlled template, anchoring a second nucleic acid construct on a second temperature-controlled template, applying a cell extract and expressing a first protein.

28. The in vitro method of sequentially expressing proteins of claim 27 wherein said first protein is released from said immobilized nucleic acid construct.

29. The in vitro method of sequentially expressing proteins of claim 28 wherein said released protein migrates to said second temperature-controlled template.

30. The in vitro method of sequentially expressing proteins of claim 29 wherein said released protein binds to a protein localized with said second anchored nucleic acid construct on said second temperature-controlled template, applying a cell extract and expressing a second protein.

* * * * *